US009151726B2

(12) United States Patent
Sun et al.

(10) Patent No.: US 9,151,726 B2
(45) Date of Patent: Oct. 6, 2015

(54) MEASUREMENT DEVICE

(75) Inventors: Tai-Ping Sun, Jhongli (TW); Tak-Shing Ching, Taichung (TW); Wei-Cheng Yeh, Nantou (TW)

(73) Assignee: National Chi Nan University, Puli, Nantou (TW)

( * ) Notice: Subject to any disclaimer, the term of this patent is extended or adjusted under 35 U.S.C. 154(b) by 290 days.

(21) Appl. No.: 13/552,168

(22) Filed: Jul. 18, 2012

(65) Prior Publication Data

US 2013/0180320 A1 Jul. 18, 2013

(30) Foreign Application Priority Data

Jan. 16, 2012 (TW) ............................ 101101588 A

(51) Int. Cl.
*G01N 27/327* (2006.01)

(52) U.S. Cl.
CPC ................................. *G01N 27/3273* (2013.01)

(58) Field of Classification Search
CPC .......... G01N 27/3273; G01N 27/3274; G01N 27/48; G01N 27/26; G01N 27/327; G01N 27/404; G01N 27/27; G01N 33/64; G01N 33/66; A61B 5/05; A61B 5/14532; A61B 5/1468–5/1482; C12Q 1/005; C12Q 1/006; C12Q 1/54
See application file for complete search history.

(56) References Cited

U.S. PATENT DOCUMENTS

2003/0109798 A1* 6/2003 Kermani ....................... 600/547
2010/0169035 A1* 7/2010 Liang et al. ..................... 702/65
2010/0305545 A1* 12/2010 Kanderian et al. ............ 604/504

OTHER PUBLICATIONS

Taiwan Patent and Trademark Office, Search Report and English Translation for TW101101588, and Cited References along with English Translations of their Abstracts for TW201142287 and TW201121178.

* cited by examiner

*Primary Examiner* — Gurpreet Kaur
(74) *Attorney, Agent, or Firm* — LeClairRyan

(57) ABSTRACT

A measurement device is for use with a current-type sensor unit, which, when applied with a driving voltage, is capable of reacting with a target substance for generating a sensor current that corresponds to a concentration level of the target substance, and includes: a driving unit operable to generate the driving voltage that includes alternating current (AC) and direct current (DC) components; and a processing unit for receiving the sensor current from the current-type sensor unit, and operable to determine the concentration level of the target substance according to a peak-to-peak value of the sensor current received by the processing unit.

6 Claims, 4 Drawing Sheets

612
7
614
615
51
62
71
72
611
73
613
61
52
3
5
6

MEASUREMENT DEVICE

CROSS-REFERENCE TO RELATED APPLICATION

This application claims priority of Taiwanese Application No. 101101588, filed on Jan. 16, 2012.

BACKGROUND OF THE INVENTION

1. Field of the Invention

The present invention relates to a measurement device, more particularly to a measurement device for measuring concentration of a target substance in a liquid sample.

2. Description of the Related Art

Referring to FIG. 1, a conventional measurement system includes a driving unit 1 for generating a driving voltage, a current-type sensor unit 2 responsive to the driving voltage for generating a sensor current that is related to a concentration level of a target substance in a liquid sample 3, and a processing unit 4 for determining the concentration level of the target substance according to a result of integration of the sensor current generated by the current-type sensor unit 2.

Referring to FIG. 2, according to a conventional configuration disclosed in U.S. Pat. No. 5,682,884, the driving unit 1 generates the driving voltage 2, which herein is a direct current voltage with a non-varying magnitude, as the current-type sensor unit 2 contacts the liquid sample 3. Theoretically, the sensor current has a magnitude that varies in a positive relation to the concentration level of the target substance. However, in practice, noise components in the sensor current may lead to reduced accuracy in the concentration level determined by the processing unit 4.

Take measurement of blood sugar as example, where the liquid sample 3 is a blood sample and the current-type sensor unit 2 is a glucose sensor. For a period of time after the driving unit 1 starts generating the driving voltage, the current-type sensor unit 2 reacts to both glucose and non-glucose substances in the liquid sample 3. Reaction of the current-type sensor unit 2 to the non-glucose substances may contribute to the noise components in the sensor current.

Referring to FIG. 3, in view of the above, U.S. Pat. No. USRE36268 discloses a conventional configuration in which generation of the driving voltage by the driving unit 1 is delayed relative to the configuration disclosed in U.S. Pat. No. 5,682,884, such that the adverse effect of the noise components in the sensor current is relatively reduced.

Referring to FIG. 4, according to a conventional configuration disclosed in U.S. Pat. No. 5,620,579, generation of the driving voltage takes place as the current-type sensor unit 2 contacts the liquid sample 3, and is subsequently paused for a predetermined time before being resumed. In this configuration, the processing unit 4 determines the concentration level of the target substance after generation of the driving voltage is resumed, thereby reducing the adverse effect of the noise components in the sensor current.

In each of the abovementioned conventional configurations, since the driving voltage is a direct current voltage, and the concentration level is determined based on a result of integration of the sensor current, accuracy of the concentration level determined by the processing unit 4 depends critically on stability of the current-type sensor unit 2 when applied with a direct current voltage. That is, if the current-type sensor unit 2 has poor stability when applied with a direct current voltage, accuracy of the concentration level thus determined will be poor.

SUMMARY OF THE INVENTION

Therefore, an object of the present invention is to provide a measurement device capable of alleviating the aforesaid drawbacks of the prior art.

Accordingly, a measurement device of the present invention is adapted for use with a current-type sensor unit, which, when applied with a driving voltage, is capable of reacting with a target substance for generating a sensor current that corresponds to a concentration level of the target substance. The measurement device includes:

a driving unit operable to generate the driving voltage that includes an alternating current (AC) component and a direct current (DC) component, and adapted to be connected electrically to the current-type sensor unit for providing the driving voltage to the current-type sensor unit; and a processing unit adapted to be connected electrically to the current-type sensor unit for receiving the sensor current from the current-type sensor unit, and operable to determine the concentration level of the target substance according to a peak-to-peak value of the sensor current received by the processing unit.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
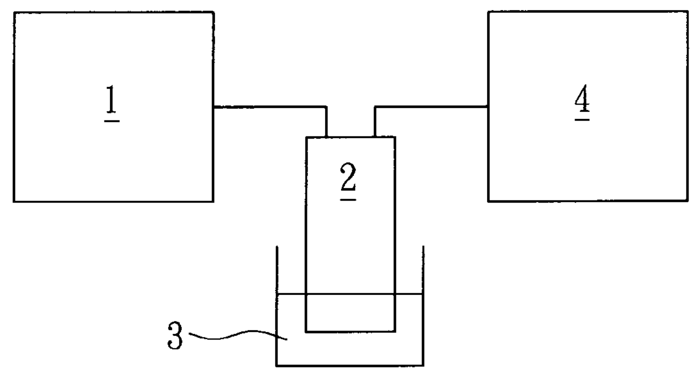
FIG. 1 is a block diagram to illustrate a conventional measurement system.
Figure 2:
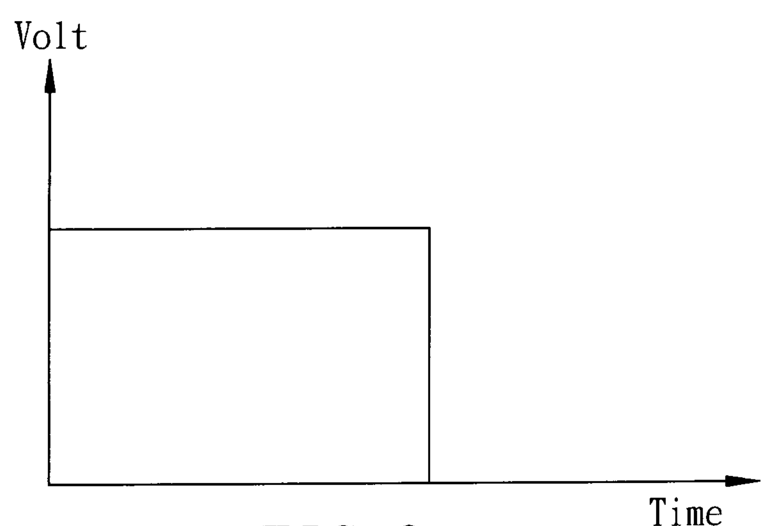
FIG. 2 is a timing diagram to illustrate a driving voltage generated according to a conventional configuration of the measurement system.
Figure 3:
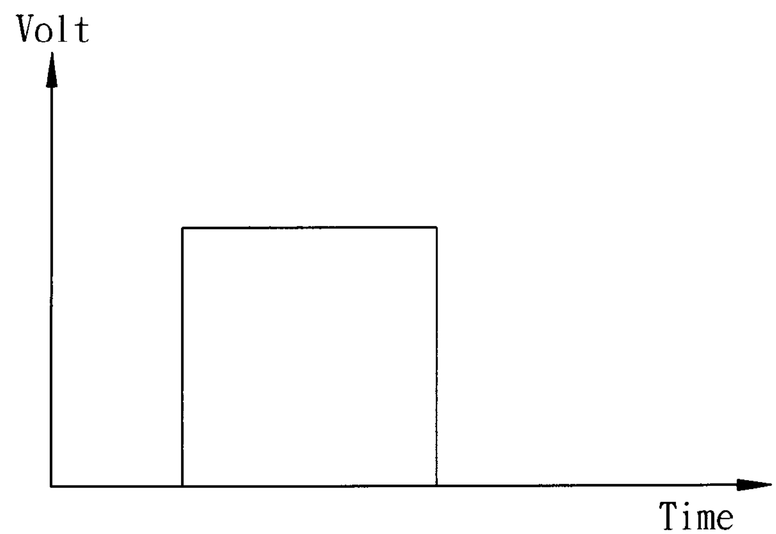
FIG. 3 is a timing diagram to illustrate a driving voltage generated according to another conventional configuration of the measurement system.
Figure 4:
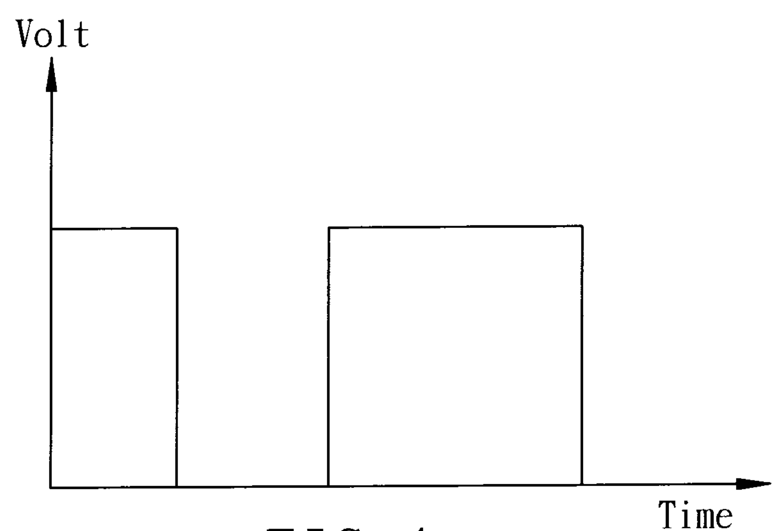
FIG. 4 is a timing diagram to illustrate a driving voltage generated according to yet another conventional configuration of the measurement system.
Figure 5:
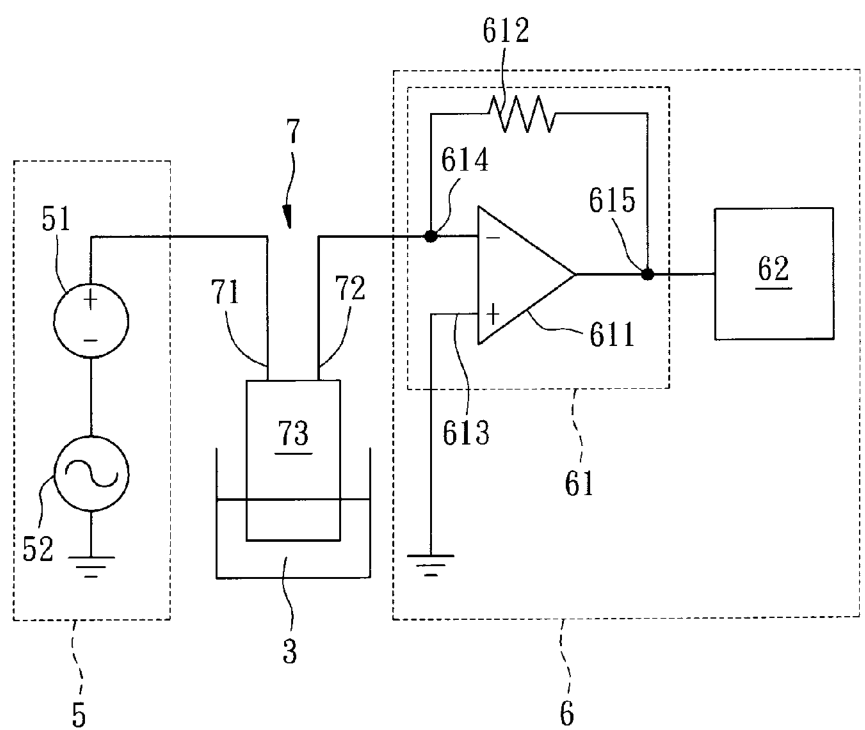
FIG. 5 is a circuit block diagram to illustrate the preferred embodiment of a measurement device according to the present invention.

Referring to FIG. 5, the preferred embodiment of a measurement device of the present invention is adapted for use with a current-type sensor unit 7 including input and output electrodes 71, 72 and a sensor portion 73, which, upon contact with a liquid sample 3, reacts to a target substance in the liquid sample 3. Such a reaction may be a reduction-oxidation reaction. The current-type sensor unit 7 may be a sensor for one of glucose, uric acid, and lactic acid, and is not limited to such.

Figure 6:
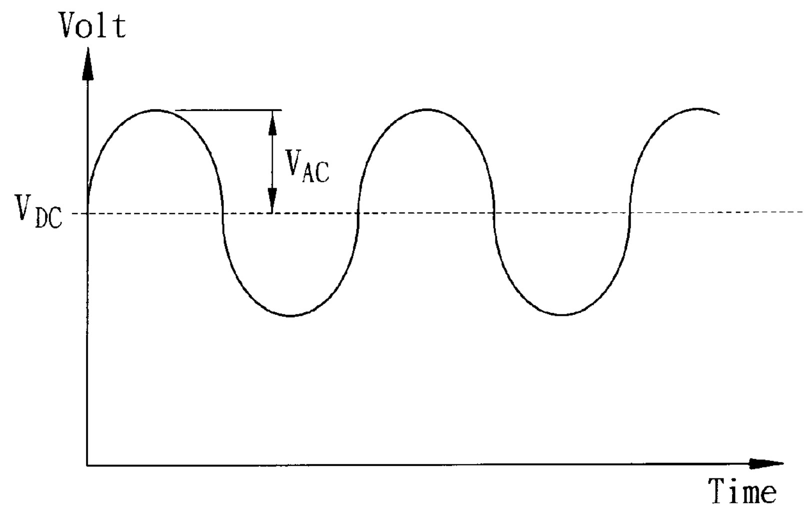
FIG. 6 is a timing diagram to illustrate a driving voltage generated by the measurement device of the preferred embodiment.

The measurement device includes a driving unit 5 and a processing unit 6. The driving unit 5 is operable to generate a driving voltage including an alternating current (AC) component and a direct current (DC) component (see FIG. 6), and is adapted to be connected electrically to the input electrode 71 of the current-type sensor unit 7 for providing the driving voltage to the current-type sensor unit 7. In the present embodiment, the driving unit 5 includes a series connection of a power supply 51 and a signal generator 52 that are interconnected between the input electrode 71 and ground, that cooperate to generate the driving voltage for provision to the current-type sensor unit 7, and that respectively contribute to the DC component and the AC component of the driving voltage.

The current-type sensor unit 7, when applied with the driving voltage, is capable of reacting with the target substance in the liquid sample 3 for generating and outputting a sensor current via the output electrode 72. The sensor current thus generated corresponds to a concentration level of the target substance in the liquid sample 3.

The processing unit 6 is adapted to be connected electrically to the output electrode 72 for receiving the sensor current from the current-type sensor unit 7, and is operable to determine the concentration level of the target substance according to a peak-to-peak value of the sensor current received by the processing unit 6. In this embodiment, the processing unit 6 includes a signal amplifying circuit 61 and a signal processing circuit 62.

The signal amplifying circuit 61 is adapted to be connected electrically to the current-type sensor unit 7 for receiving the sensor current from the current-type sensor unit 7, and is operable to convert the sensor current into a sensor voltage. In this embodiment, the signal amplifying circuit 61 includes a resistor 612 and an operational amplifier 611. The operational amplifier 611 has an inverting input terminal 614 that is adapted to be connected electrically to the output electrode 72 for receiving the sensor current from the current-type sensor unit 7, a grounded non-inverting input terminal 613, and an output terminal 615 that is connected electrically to the inverting input terminal 614 via the resistor 612. The operational amplifier 611 is operable to generate the sensor voltage based on the sensor current received by the operational amplifier 611 for output to the signal processing circuit 62 via the output terminal 615. In this embodiment, the driving voltage generated by the driving unit 5 is a positive voltage relative to the non-inverting input terminal 613 of the operational amplifier 611.

The signal processing circuit 62 is connected electrically to the output terminal 615 of the operational amplifier 611 of the signal amplifying circuit 61 for receiving the sensor voltage from the signal amplifying circuit 61, and is operable to determine the concentration level of the target substance according to a peak-to-peak value of the sensor voltage received by the signal processing circuit 62.

Specifically, in this embodiment, the signal processing circuit 62 is operable to determine, based on relationships 1 and 2, a peak-to-peak value of a correction current according to the peak-to-peak value of the sensor voltage received by the signal processing circuit 62 and a predetermined correction value.

$$V_{o[G]} = V_{I[G]} - V_2 \tag{1}$$

$$I_{o[G]} = \frac{V_{o[G]}}{R_f} \tag{2}$$

where $V_{O[G]}$ is a peak-to-peak value of a correction voltage, $V_{I[G]}$ is the peak-to-peak value of the sensor voltage, $V_2$ is the predetermined correction value, $R_f$ is a resistance of the resistor 612, and $I_{O[G]}$ is the peak-to-peak value of the correction current.

Next, the signal processing circuit 62 is operable to determine, based on relationship 3, the concentration level of the target substance according to a result of division of the peak-to-peak value of the correction current by a predetermined sensitivity value.

$$[G] = \frac{I_{o[G]}}{S}$$

where S is a predetermined sensitivity value, and [G] is the concentration level of the target substance.

It is worth noting that the predetermined correction value ($V_2$) is a peak-to-peak value of the sensor voltage when the driving voltage is applied to the current-type sensor unit 7 and when the sensor portion 73 is not in contact with any target substance. Further, the sensitivity value (S) is predetermined based on a result of division of a peak-to-peak value of a correction current corresponding to a liquid sample 3 with a known concentration level of the target substance by the concentration level of the target substance.

Preferably, the measurement device is configured such that the signal processing circuit 62 determines the peak-to-peak value of the correction current based on an average of peak-to-peak values of the sensor voltage, which correspond temporally and respectively to a plurality of periods of the AC component of the driving voltage, during a predetermined time after the driving unit 5 starts providing the driving voltage to the current-type sensor unit 7. That is, the peak-to-peak value of the correction voltage ($V_{O[G]}$) is determined based on the average of the peak-to-peak values of the sensor voltages during the predetermined time after the driving unit 5 starts providing the driving voltage to the current-type sensor unit 7. The periods of the AC component to which the peak-to-peak values of the sensor voltage correspond may be consecutive or otherwise.

It is worth noting that, as a result of a change in frequency of the AC component of the driving voltage, a difference between current sensitivity values (S) predetermined for different liquid samples 3 with different known concentration levels of the target substance may also change. Therefore, it may be preferable that an optimal frequency of the AC component of the driving voltage corresponding to a particular current-type sensor unit 7 be predetermined during a design phase of the measurement device, such that the difference between the current sensitivity values (S) thus predetermined for the different liquid samples 3 with the different known concentration levels of the target substance is minimal.

In the prior art, since the driving voltage merely includes the DC component, the current sensitivity value (S) is limited by stability of the current-type sensor unit 7, and is not adjustable. In contrast, the driving voltage, according to the present invention, has an adjustable frequency for adjustment according to a target sensitivity value (S). Thus, it is possible to optimize stability of a particular current-type sensor unit 7 and to improve accuracy of the concentration level of the target substance determined by the processing unit 6 through optimizing the frequency of the AC component of the driving voltage.

Figure 7:
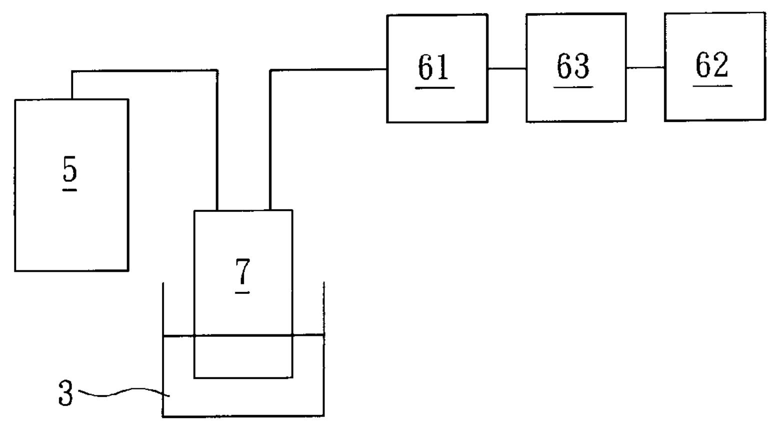
FIG. 7 is a block diagram to illustrate a modification of the preferred embodiment.

Referring to FIG. 7, to further improve accuracy of the concentration level determined by the processing unit 6, the processing unit 6 may be modified to include a filter 63 connected electrically between the signal amplifying circuit 61 and the signal processing circuit 62 for removing frequency components, that do not correspond substantially to frequency of the AC component of the driving voltage, from the sensor voltage received by the signal processing circuit 62.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A measurement device adapted for use with a current-type sensor unit, which, when applied with a driving voltage, is capable of reacting with a target substance for generating a sensor current that corresponds to a concentration level of the target substance, said measurement device comprising:

a driving unit configured to generate the driving voltage that includes an alternating current (AC) component and a direct current (DC) component, and adapted to be connected electrically to the current-type sensor unit for providing the driving voltage to the current-type sensor unit; and a processing unit adapted to be connected electrically to the current-type sensor unit for receiving the sensor current from the current-type sensor unit, and configured to determine the concentration level of the target substance according to a peak-to-peak value of the sensor current received by said processing unit;

wherein said processing unit includes:

a signal amplifying circuit adapted to be connected electrically to the current-type sensor unit for receiving the sensor current from the current-type sensor unit, and configured to convert the sensor current into a sensor voltage; and a signal processing circuit connected electrically to said signal amplifying circuit for receiving the sensor voltage from said signal amplifying circuit, and configured to determine the concentration level of the target substance according to a peak-to-peak value of the sensor voltage, to determine a peak-to-peak value of a correction current according to the peak-to-peak value of the sensor voltage and a predetermined correction value, and to subsequently determine the concentration level of the target substance according to a result of division of the peak-to-peak value of the correction current by a predetermined sensitivity value.

2. The measurement device as claimed in claim 1, wherein said driving unit includes a series connection of a power supply and a signal generator that cooperate to generate the driving voltage, and that respectively contribute to the DC component and the AC component of the driving voltage.

3. The measurement device as claimed in claim 1, wherein said signal processing circuit is configured to determine the peak-to-peak value of the correction current based on an average of the peak-to-peak value of the sensor voltage during each cycle within a predetermined time after said driving unit starts providing the driving voltage to the current-type sensor unit.

4. The measurement device as claimed in claim 1, the current-type sensor unit including input and output electrodes for receiving the driving voltage and outputting the sensor current therethrough, respectively, wherein:

said driving unit is adapted to be connected electrically to the input electrode for providing the driving voltage to the current-type sensor unit therethrough; and said signal amplifying circuit includes a resistor, and an operational amplifier having a first input terminal that is adapted to be connected electrically to the output electrode for receiving the sensor current from the current-type sensor unit, a grounded second input terminal, and an output terminal that is connected electrically to said first input terminal via said resistor and that is connected electrically to said signal processing circuit, said operational amplifier being configured to generate the sensor voltage based on the sensor current received by said operational amplifier for output to said signal processing circuit via said output terminal.

5. The measurement device as claimed in claim 4, wherein said second input terminal of said operational amplifier is a non-inverting input terminal, and the driving voltage generated by said driving unit is a positive voltage relative to said second input terminal of said operational amplifier.

6. The measurement device as claimed in claim 1, wherein said processing unit further includes a filter connected electrically between said signal amplifying circuit and said signal processing circuit for removing frequency components, that do not correspond to the AC component of the driving voltage, from the sensor voltage received by said signal processing circuit.

* * * * *